Figure 1:
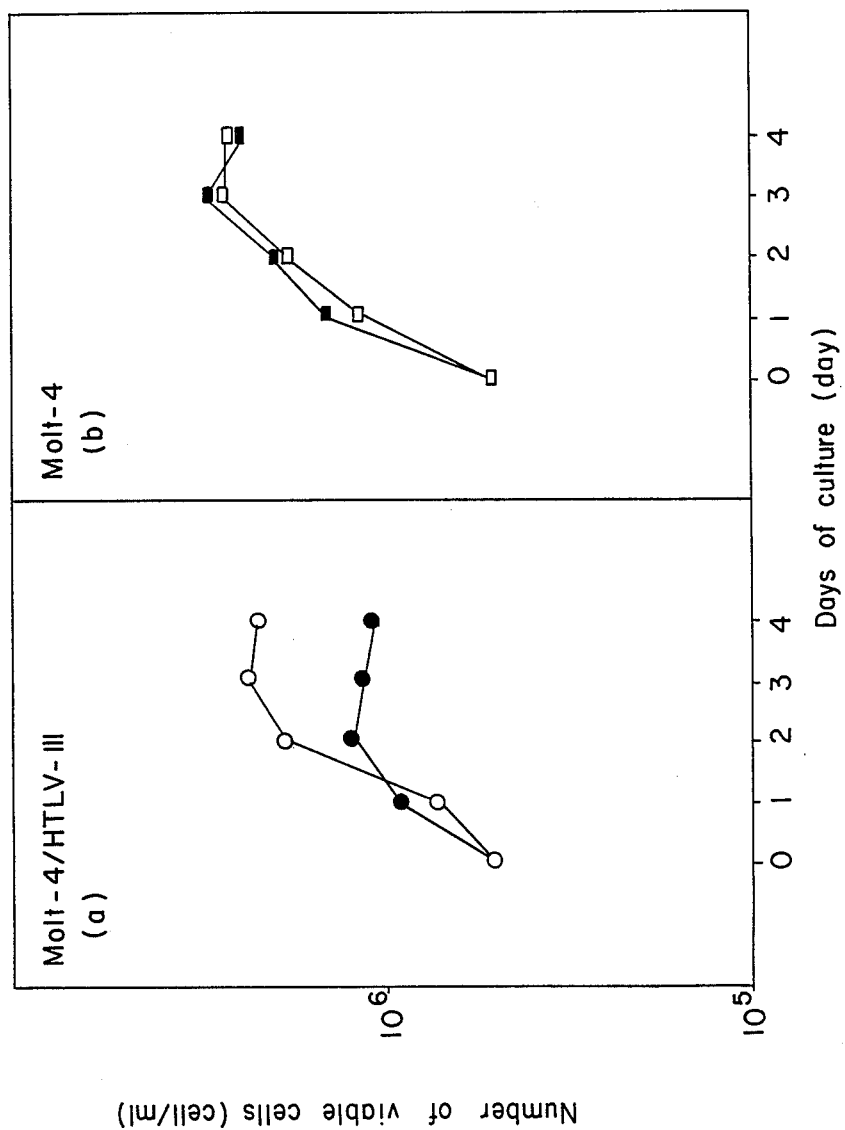
Figure 2:
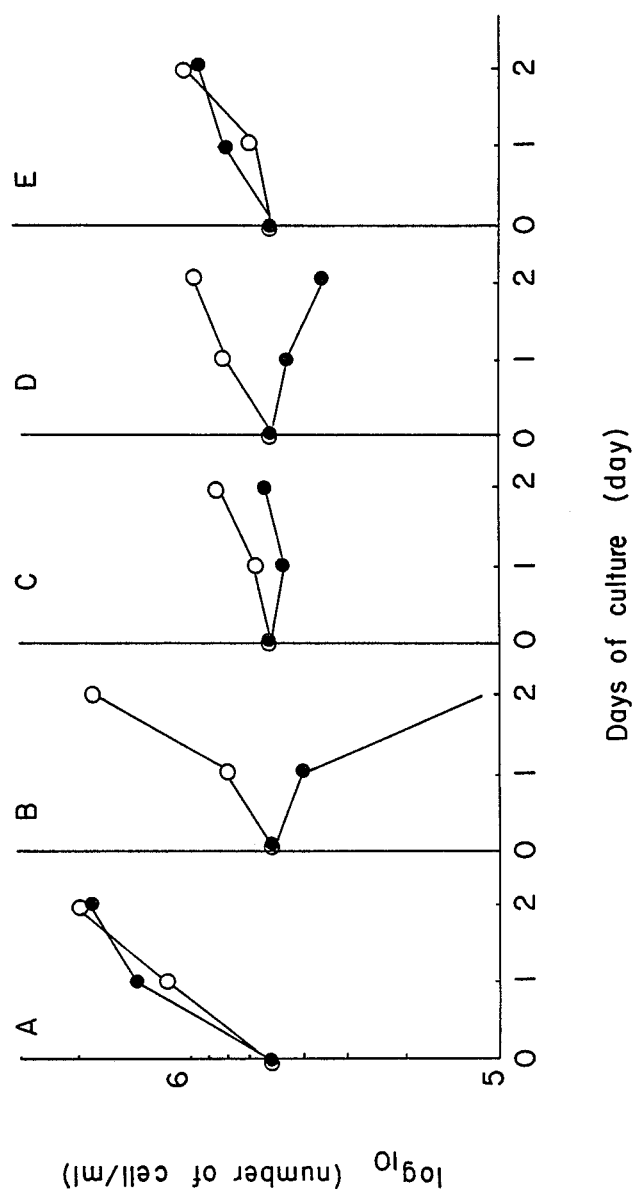
Figure 3:
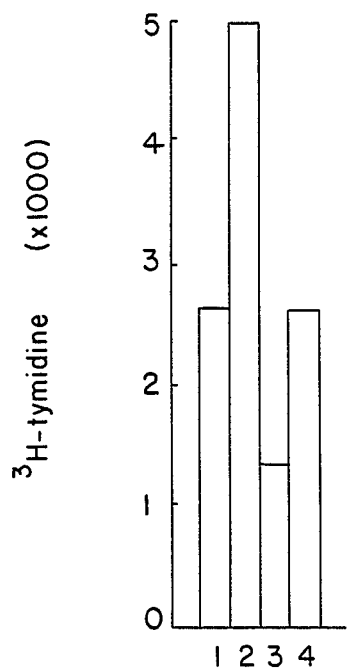

United States Patent [19]

Ueda et al.

[11] Patent Number: 4,867,976
[45] Date of Patent: Sep. 19, 1989

[54] H.I.V. TREATMENT UTILIZING SPECIFIC INHIBITATION OF PROTEIN SYNTHESES IN A CELL

[75] Inventors: Shigeharu Ueda; Kazuyoshi Ikuta; Shiro Kato; Tsuyoshi Uchida, all of Osaka, Japan

[73] Assignee: Sumitomo Chemical Company, Limited, Osaka, Japan

[21] Appl. No.: 69,695

[22] Filed: Jul. 2, 1987

[30] Foreign Application Priority Data

May 22, 1987 [JP] Japan ................... 62-126794

[51] Int. Cl.$^4$ .............. A61K 39/02; A61K 39/05; A61K 39/21; A61K 37/00
[52] U.S. Cl. ..................... 424/92; 424/93; 530/350; 530/825; 530/826; 530/827; 530/828; 530/829; 530/830; 514/2; 514/21; 514/885
[58] Field of Search .......... 530/350, 362, 825, 826, 530/828, 827, 829, 830; 424/92, 93

[56] References Cited

U.S. PATENT DOCUMENTS 4,638,049  1/1987  Masuho et al. .
4,709,017  11/1987  Collier et al. .

FOREIGN PATENT DOCUMENTS 0240346  10/1987  European Pat. Off. .
0247873  12/1987  European Pat. Off. .

OTHER PUBLICATIONS

Uchida et al., "J. Cell Biology", vol. 80, pp. 10–20, (1979).
Nakanishi et al., "Exp. Cell Res.", 159, pp. 399–409, (1985).
Uchida et al., "Exp. Cell Research", 152, pp. 313–321, (1984).
Ueda et al., "Exp. Cell Research", 132, pp. 259–263, (1981).
Jansons et al., "Biochimica et Biophysica Acta", 735, pp. 433–437, (1983).
McIntosh et al., "Biochimica et Biophysica Acta", 690, pp. 224–230, (1982).
Norrie et al., "Analytical Biochemistry", 127, pp. 276–281, (1982).
Alving et al., "Proc. Natl. Acad. Sci. U.S.A.", vol. 77, No. 4, pp. 1986–1990, (1980).
Boquet, "Eur. J. Biochem.", 100, pp. 483–489, (1979).

*Primary Examiner*—John Kight
*Assistant Examiner*—C. Azpuru
*Attorney, Agent, or Firm*—Birch, Stewart, Kolasch & Birch

[57] ABSTRACT

A method for treatment of acquired immuno-deficiency syndrome (AIDS) which comprises administering a therapeutically effective amount of liposomes containing a toxin which specifically inhibits the protein synthesis in cells to a patient with AIDS.

5 Claims, 4 Drawing Sheets

Days of culture (day)

H.I.V. TREATMENT UTILIZING SPECIFIC INHIBITATION OF PROTEIN SYNTHESES IN A CELL

The present invention relates to the treatment of acquired immunodeficiency syndrome (AIDS). More particularly, the invention relates to a therapeutic agent for treatment of AIDS.

AIDS, which is caused by infection with human immunodeficiency virus (HIV), is causing serious social problems in the world, and various therapeutic agents for treatment of AIDS are under development, of which typical examples are interferon, interleukin, azidothimidine (AZT), etc. However, their therapeutic effects are still not sufficiently reliable and effective.

Diphtheria toxin is a single chain protein having a molecular weight of about 60,000. This toxin exerts strong cytotoxicity against human beings, and its lethal dose for an adult is from about 10 to 20 $\mu$g. Restricted decomposition of the toxin by treatment with trypsin in the presence of a reducing agent under a mild condition gives fragment A having a molecular weight of about 20,000 and fragment B having a molecular weight of about 40,000 (Collier, R. J. et al. (1971), I. Thiol-dependent dissociation of a fraction of toxin into enzymatically active and inactive fragments, J.Biol.Chem 246:1496-1503; Gill, D. M. et al. (1971), Observations on the structure of diphtheria toxin, J. Bio.Chem., 246:1485-1491). The fragment A inhibits the protein synthesis in cells causing killing of the cells, while fragment B performs a role of introducing fragment A into cells through the binding onto the surfaces of the cells. Thus, the cytotoxicity of diphtheria toxin is produced from the combination of fragments A and B, and each of fragments A and B does not exert any material cytotoxicity by itself (Uchida, T. et al (1972), Reconstitution of diphtheria toxin from two nontoxic cross-reacting mutant toxins, Science 175:901-903). In other words, fragment A alone, which is not accompanied by fragment B, does not exert any material cytotoxicity outside cells, and its cytotoxicity is less than $10^{-4}$ of that of diphtheria toxin. When, however, fragment A is once introduced into a cell by any artificial means, its one molecule is sufficient to kill the cell (Yamaizumi, M. et al. (1978), One molecule of diphtheria toxin fragment A introduced into a cell can kill the cell, Cell, 15:245-250).

Inhibition of the protein synthesis by fragment A is made through its catalyzation on the following reaction (1) to inactivate elongation factor 2 (EF-2), which is a proteinous factor essential for elongation of a peptide chain. In the elongation process, peptidyl t-RNA is transferred from the A site to the P site (Honjo, T. et al. (1968), Diphtheria-toxin-dependent adenosine diphosphate ribosylation of aminoacyl transferase II and inhibition of protein synthesis, J.Biol.Chem. 243:3553-3555):

$$EF\text{-}2 + NAD^+ \rightarrow ADP\text{-}Ribose\text{-}EF2 + Nicotinamide + H^+ \quad (1)$$

According to the reaction (1), EF-2 bonds covalently to ADP-Ribose and is inactivated, whereby the protein synthesis is inhibited. The above reaction is highly specific, and any substrate other than EF-2 has not been found by the present time.

When liposomes containing fragment A are injected into the brain of an animal with viral encephalitis, the fragment is selectively introduced into enveped virus-infected cells so that the protein synthesis in such cells is completely inhibited, resulting in destruction of said infected cells. Simultaneously, the proliferation of virus as well as the extension of infection is prevented. Accordingly, the liposomes are useful for treatment of viral encephalitis such as subacute sclerosing panencephalitis, measles encephalitis and herpetic encephalitis (Japanese Patent Publication (Unexamined) No. 252425/85).

In addition to fragment A of diphtheria toxin, there have been known a certain number of toxins which specifically inhibit the protein synthesis of a cell. The C-terminal active portion of Pseudomonas exotoxin and fragment A derived from castor oil plant seeds are examples of such toxins.

In order to develop an effective method for treatment of AIDS, the present inventors have intensively studied and, as a result, have found that liposomes containing a toxin specifically inhibiting the protein synthesis in a cell, especially fragment A of diphtheria toxin, can attack and kill selectively HIV-infected cells, and that the liposomes are quite useful as a therapeutic agent for the treatment of AIDS. This invention is based on the above finding.

Accordingly, the present invention provides a method for the treatment of AIDS which comprises administering a therapeutically effective amount of liposomes containing a toxin which specifically inhibits the protein synthesis of a cell to a patient of AIDS. It also provides a therapeutic agent for treatment of AIDS which comprises liposomes containing a toxin specifically inhibiting the protein synthesis in a cell.

In the present invention, the fragment A of diphtheria toxin is preferably used as the toxin specifically inhibiting the protein synthesis in a cell, but such known toxins as the C-terminal active portion of Pseudomonas exotoxin or fragment A derived from castor oil plant weeds can also be used.

This invention will be hereinafter explained taking Fragment A of diphtheria toxin (hereinafter referred to as "fragment A") as a representative example. The scope of the invention is not limited to only the case wherein liposomes containig fragment A of diphtheria toxin are used but should be understood to cover the case wherein liposomes containing other toxins specifically inhibiting the protein synthesis in a cell are used.

As stated above, fragment A of diphtheria toxin is obtainable from diphtheria toxin by a conventional procedure, For instance, diphtheria toxin as produced by Corvnebacterium diphtheriae is treated with trypsin in the presence of a reducing agent, and the restrictively decomposed product is purified to recover fragment A. Further, for instance, cultivation of a fragment A-producing mutant C7 (beta 22) of Corynebacterium diphtheriae gives fragment A alone, i.e. not contaminated with fragment B (Uchida, et al., (1979), Reconstitution of lipid vesicles associated with HVJ (Sendai virus) spikes; Purification and some properties of vesicles containing nontoxic fragment A of diphtheria toxin, J.Cell Biol. 80:10-20). The mutant C7 (beta 22) is available from the Division of Cellular Biology, Institute for Molecular and Cellular Biology, Osaka University, located at Suita, Osaka, Japan.

The liposomes themselves can be readily prepared by a known method. In a typical example, the liposomes may be prepared from a phospholipid, preferably lecithin, and cholesterol. Phosphatidylserine or phosphatidylethanolamine may be added thereto. The mixing proportion of the phospholipid cholesterol is not limitative insofar as the resulting mixture can maintain the form of liposomes at a low temperature, for instance, about 0° to 10° C., and it may be usually from about 1:5 to 1:8 by weight. The weight proportion of phosphatidylserine and/or phosphatidylethanolamine, if added, may be about ½-⅓ (preferably about ½) of the used cholesterol.

For preparation of the fragment A-containing liposomes, the phospholipid and cholesterol may be admixed with fragment A in a small quantity of 0.01 M phosphate buffer containing 0.5 % by weight of a nonionic surfactant (e.g. octylglycoside, "Nonydet P40") and 0.25–0.3 M sucrose, followed by removal of the removal of the surfactant by a conventional separation procedure such as dialysis, gel filtration or adsorption. The weight of fragment A to be admixed may be usually from about 1 to 1/5 of that of the phospholipid. Fragment A not contained in the liposomes can be eliminated by gel filtration using a gel filtration agent, preferably "Bio-Gel" A50m (manufactured by Bio Rad).

The prepared fragment A-containing liposomes can be used for the treatment or prevention of diseases caused by HIV. For such purpose, the fragment A-containing liposomes may be administered intravenously to each patient, for example, at a dose of 1 to 5 ml once a week. The dose may be appropriately varied with the symptom, the bodyweight, etc.

It has been found that AZT effectively prevents HIV-uninfected cells from infection with HIV derived from the infected cells or free HIV remaining after the treatment with the liposomes of the invention. Thus, the combined use of the fragment A-containing liposomes with AZT is particularly effective in preventive or therapeutic treatment of AIDS.

When HIV-infected cells are cultured in a medium containing the fragment A-containing liposomes, fragment A is introduced into the cells so that all the protein syntheses in the cells are inhibited, and as the result, the cells are killed. It is noted that the proliferation of HIV is thus inhibited, and the extension of the infection is prevented.

It is considered that the fragment A-containing liposomes cannot reach to the lipid bilayer of the plasmic membrane in HIV-uninfected cells, and that, in the case of HIV-infected or HIV-producing cells, HIV infection and/or production changes the surface structure of the cells so that the fragment A-containing liposomes can reach to the lipid bilayer at the cell surface. Presumably, because of this reason, the fragment A-containing liposomes are considered to exert cytotoxicity selectively on HIV-infected or HIV-producing cells.

The anti-HIV antibody which can recognize an env protein in HIV does not affect the cytotoxicity of the fragment A-containing liposomes to HIV-infected cells. This means that HIV-infected or HIV-producing cells in AIDS patients having the HIV antibody or HIV-infected persons can be killed by treatment with the fragment A-containing liposomes.

Since HIV-infected or HIV-producing cells in AIDS patients or HIV-infected persons are mainly present in their bloods, it seems to be quite easy to act the fragment A-containing liposomes onto the cells. Thus, the fragment A-containing liposomes of the invention exert an excellent preventive or therapeutic effect in the treatment of AIDS. More specifically, the fragment A-containing liposomes of the invention are characteristic in exerting an excellent preventive or therapeutic effect for AIDS without giving unfavorable influence on uninfected normal cells.

The preparation procedures of the liposomes of the invention will be hereinafter explained more in detail taking fragment A of diphtheria toxin as a representative example. For the preparations of liposomes containing other toxins, substantially the same procedures can be used.

Preparation of fragment A of diphtheria toxin:

The mutant C7 (beta 22) of *Corynebacterium diphtheriae* is cultured in a nutrient medium. The cells are removed from the culture medium by centrifugation. To the supernatant is added ammonium sulfate to precipitate fragment A. The precipitated fragment A is collected, dialyzed to remove ammonium sulfate, adsorbed on DEAE-cellulose and eluted therefrom using NaCl solutions having gradient concentrations, whereby fragment A almost free from any contaminant is obtained. Final purification is made by gel-filtration using G-150. The yield of fragment A as the purified product from about 5 liters of the supernatant is about 20 mg.

Preparation of liposomes containing fragment A of diphtheria toxin:

A mixture of lecithin and cholesterol (5 : 1 by weight) is added to 0.01 M tris buffer (pH 7.5) to make a concentration of 2 mg/ml. Then, fragment A is added to make a concentration of 1 mg/ml to 500 μg/ml. The resultant mixture is stirred well, and "Nonidet" P40 (NP40) is added thereto to make a concentration of 0.5 % by weight. Instead of NP40, alkylphenol polyoxyethylene ether ("Triton" X100, manufactured by Rohm & Haas) may be used. On addition of such neutral surfactant, the lipid is solubilized to give a clear solution. Removal of the neutral surfactant from the clear solution gives liposomes containing fragment A. In the case of using NP40, dialysis is effected by the aid of a dyalizing tube ("Spectrapore" No. 2; manufactured by Spectrum Medical Industries, Inc.) to remove NP40. In the case of using "Triton" X 100, stirring is carried out in the presence of "Bioheads" SM2 (manufactured by Bio Rad) so that "Triton" X 100 is adsorbed on "Bioheads". In order to remove fragment A not contained in the liposomes, the product is treated with "Bio-Gel" A50m (manufactured by Bio Rad). The thus obtained suspension of the purified fragment A-containing liposomes contains fragment A in an amount of 2 to 5 μg/ml.

This invention will be hereinafter explained more in detail by way of examples. However, these examples should not be construed to limit the scope of the invention thereto and are to be understood merely for the purpose of illustration.

EXAMPLE 1

A test tube containing HIV-producing human cells (Molt-4/HTLV III) ($5 \times 10^6$ cells) was subjected to centrifugation, and the supernatant was removed. A medium (RPMI-1640 containing 10% fetal calf serum) (1 ml) was added thereto to make a cell suspension. The suspension was divided into two 0.5 ml portions, of which one was combined with 0.35 ml of phosphate buffered saline (PBS) alone, and liposomes containing fragment A of diphtheria toxin (fragment A content, 1.40 μg). Both of them were kept on a $CO_2$-incubator (37° C., 5% $CO_2$) for 1.5 hours, and then 5 ml of a fresh medium (RPMI-1640 containing 10% fetal calf serum) was added thereto. The number of cells was counted daily and plotted to give proliferation profiles as shown in FIG. 1 of the accompanying drawings.

The same procedure as above was repeated using virus-uninfected Molt-4 in place of Molt-4/HTLV-III.

In FIG. 1 wherein the abscissa indicates the day of culture and the ordinate indicates the number of cells, (a) and (b) show respectively the case with Molt-4/HTLV-III wherein –●– is the fragment A-containing liposomes added and –○– is the fragment A-containing liposomes not added and the case with Molt-4 wherein –■– is the fragment A-containing liposomes added and –□– is the fragment A-containing liposomes not added. In the case of virus-infected cells (Molt-4/HTLV-III), apparent suppression of cell Proliferation was produced by the addition of the fragment A-containing liposomes. In case the of virus-uninfected cells (Molt-4), the substantially same proliferation profile was obtained irrespective of addition of the fragment A-containing liposomes. The above results indicate that proliferation of virus-infected cells was specifically inhibited by the fragment A-containing liposomes.

EXAMPLE 2

A mixture of lecithin and cholesterol (5:1 by weight) was admixed with fragment A of diphtheria toxin (5 mg). The resultant mixture was solubilized with 0.5% NP40 in 1 ml of 0.01 M phosphate buffer (pH 7.2) containing 0.3 M sucrose. Then, the mixture was dialyzed against the same buffer as above at 0° to 1° C. for several days and subjected to gel filtration with "Bio-Gel" A50m to remove fragment A not contained in liposomes, whereby liposomes containing fragment A of diphtheria toxin was obtained.

HIV-uninfected cells and HIV-producing cells of acute lymphocyte leukemia (ALL) derived cells, Molt-4 and Tall-1, and also HTLV I-infected cells (MT-4) were cultured in media (RPMI-1640 containing 10 % fetal calf serum). Each of the cell cultures (cell concentration $2.5\times10^6$ cells/ml) was admixed with a suspension of the fragment A-containing liposomes (concentration of fragment A, 3.33 μg/ml) (0.19 $OD_{540nm}$) or the same volume of PBS as control. The obtained mixture was incubated under shaking at 37° C. for 2 hours, diluted with RPMI-1640 containing 10% fetal calf serum to make a cell concentration of $5\times10^5$ cells/ml and incubated at 37° C. in a $CO_2$-incubator. The number of cells was counted every 24 hours for two days. In the above procedure, there were used two HIV, i.e. HTLV-III isolated in U.S.A. and LAV isolated in France (Popovic, M. et al., Science, 224, 497 (1987); Levy, J.A. et al., ibid,, 225 840 (1984); Barre-Sinoussi, A. et al., ibid, 220, 868 (1983)).

The results are shown in FIG. 2 wherein the abscissa indicates the day of culture and the ordinate indicates the number of cells. A, B, C, D and E show the case with HTLV-III-producing cells (Molt-4/HTLV-III), the case with HIV-uninfected cells (Tall-1), the case with HIV-producing cells (Tall-1/LAV) and the case with HTLV-1-infected cells (MT-4), and in those cases, -●- indicates the fragment A-containing liposomes added and -○- indicates PBS added. The fragment A-containing liposomes showed no toxicity against HIV-uninfected cells (Molt-4) and HTLV-1-infected cells (MT-4) (FIG. 2, A and E), while they showed slight toxicity against virus-uninfected (Tall-1) (FIG. 2, C). In the case of HTLV-III-producing cells (Molt-4/HTLV-III), the number of cells decreased to 6.2% of that in control (treated with PBS) after treatment with the fragment A-containing liposomes (FIG. 2, B). Similarly, in the case of HIV-producing cells (Tall-1/LAV), the number of cells decreased to 40.0% of that in control (FIG. 2, D).

From these results, it is clear that the surface structure of ALL-derived cells became sensitive to the fragment A-containing liposomes by HIV production and that the fragment A-containing liposomes exert a selective cytotoxicity against HIV-producing cells.

EXAMPLE 3

MT-4 cells were infected with HIV obtained from a culture of Molt-4/HTLV-III cells and then cultured for 2 days. In the same manner as in Example 2, the resulting cells were treated with the fragment A-containing liposomes. Control was treated with PBS.

Then, each of the suspensions of cells adjusted to a cell concentration of 5 x $10^5$ cells/ml was cultured in the presence of absence of AZT (5 um) in a medium (RPMI-1640) containing 10% fetal calf serum) at 37° C. for 24 hours. Cell activity was measured by the incorporation of $^3$H-thimidine. Thus, the cells in 200 μl of each cell suspension were pulse-labeled with 10 μl of $^3$H-thymidine (40 μCi/ml) (manufactured by Amersham, 23 Ci/mmol) for 2 hours, and $^3$H-thymidine incorporation was determined by counting trichloroacetic acid (TCA)-insoluble radioactivity.

The results are shown in FIG. 3 wherein the ordinate indicates the amount of $^3$H-thymidine incorporation into HIV-infected cells (MT-4), and 1, 2, 3 and 4 correspond respectively to the case wherein treatment was made with the fragment A-containing liposomes but not with AZT, the case wherein treatment was made with the fragment A-containing liposomes and also with AZT, the case wherein treatment was made with PBS but not with AZT and the case wherein treatment was made with PBS and also with AZT.

From FIG. 3, it is understood that $^3$H-thymidine incorporation into the cells treated with the fragment A-containing liposomes (1, 2) is greater than that into the cells treated with PBS (3). The maximum $^3$H-thymidine incorporation was observed in the cells treated with the fragment A-containing liposomes and with AZT. These results suggest that the surface structure of MT-4 cells became sensitive to the binding with the fragment A-containing liposomes as the result of HIV infection and that AZT inhibits infection of uninfected MT-4 cells with cell-derived or free HIV remaining after treatment with the fragment A-containing liposomes.

EXAMPLE 4

The effect of the anti-HIV antibody on the treatment with the fragment A-containing liposomes was examined, and the results are shown in FIG. 4 wherein the abscissa indicates the day of culture and the ordinate indicates the cell concentration.

Namely, Molt-4/HTLV-III cells were treated with a 500-fold dilution of the serum of AIDS virus-infected patients (IF titer: 1:4096) at 37° C. for 2 hours. The resulting cells, i.e. antibody-treated Molt-4/HTLV-III cells, and antibody-untreated Molt-4/HTLV-III cells were treated with the fragment A-containing liposomes (fragment A concentration, 3.57 μg/ml) (0.33 $OD_{540\,nm}$) (—●—). As control, each of the cells was also treated with the liposomes (0.33 $OD_{540\,nm}$) not containing fragment A (—▲—), fragment A alone (concentration, 1.67 μg/ml) (—■—), a mixture of the liposomes (0.33 OD$_{540\ nm}$) not containing fragment A and fragment A (concentration, 1.67 ug/ml) (—▲—) or PBS (—○—). Further, untreated and uninfected cells (Molt-4) were treated with the fragment A-containing liposomes or PBS. The cell numbers were counted every 24 hours for 4 days.

Figure 4:
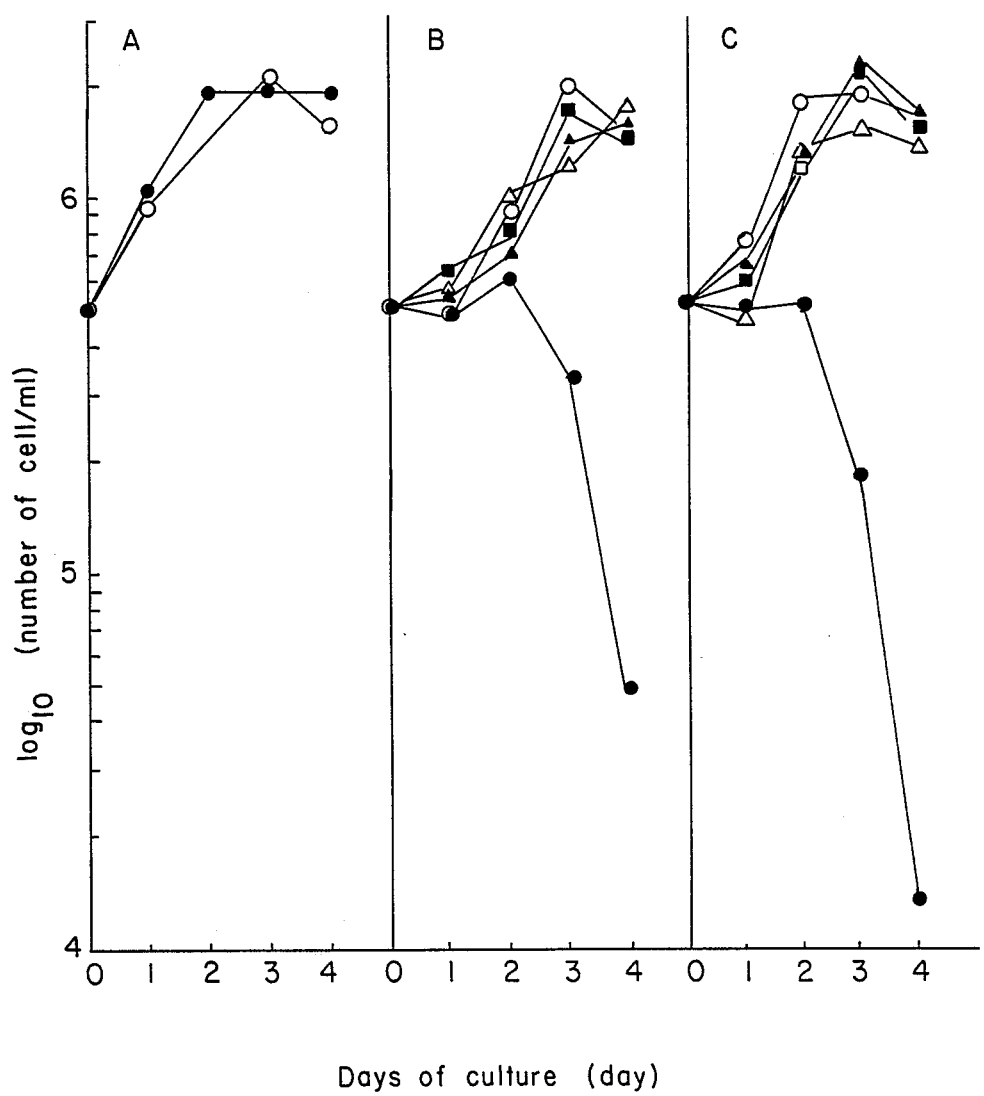

In FIG. 4, A, B and C correspond respectively to the case with antibody-untreated and HIV-uninfected cells (Molt-4), the case with antibody-untreated and HTLV-III-producing cells (Molt-4/HTLV-III) and the case with antibody-treated and HTLV-III-producing cells (Molt-4/HTLV-III).

As understood from FIG. 4, the cytotoxcity on Molt-4/HTLV-III cells was observed only when treated with the fragment A-containing liposomes (FIG. 4, B). The anti HIV-antibody gave no influence on the cytotoxicity of the fragment A-containing liposomes (FIG. 4, C). The fragment A-containing liposomes showed no toxic effect on uninfected cells (FIG. 4, A).

EXAMPLE 5

On the 3rd day after treatment with one of the fragment A-containing liposomes and four kinds of control fluids as used in Example 4, the infectious virus titers of the Molt-4/HTLV-III cell culture medium and the cell fraction were determined by the immunofluorescence (IF) procedure using a 1000-fold dilution of the serum of AIDS virus-infected patients (IF titer, 1:4096). The cell suspension was fractionated into the cells and the culture medium, and the fractionated cells were suspended in a culture medium having the same volume as the original culture medium. The TCID$_{50}$/ml value of each specimen was measured using MT-4 cells. MT-4 cells (1×10$^6$ cells/ml; 100 μl) were placed into each flat well of a microplate and inoculated with the same volume of each of serial 10-fold dilutions of the culture medium or the cell suspension as the specimen. After incubation at 37° C. for 5 days, the cells were smeared, fixed with cold acetone for 10 minutes and labeled with anti-HIV serum. The Reed and Meunch method was used for determination of the 50 percent end point (Reed, L. J. et al., Am.J.Hyg., 27, 493 (1938)). The results are shown in Table 1.

The infectious virus titer of the culture medium of Molt-4/HTLV-III cells treated with the fragment A-containing liposomes after fractionation of the cells therefrom was reduced to 4.6% of that in the case treated with a mixture of the liposomes not containing fragment A and fragment A. As to the cell fraction, the HIV infectivity of the HIV-infected cells treated with the fragment A-containing liposomes decreased to 1.0% of that of the HIV-infected cells treated with a mixture of the liposomes not containing fragment A and fragment A. The HIV infectivity of the culture medium and the cells treated with other control fluids such as the liposomes not containing fragment A, fragment A or PBS were nearly equal to that of the case treated with a mixture of the liposomes not containing fragment A and fragment A. The similar results were obtained on Molt-4/HTLV-III cells treated with anti-HIV antibody. The culture medium of Molt-4/HTLV-III cells treated with anti-HIV antibody gave somewhat a low infectious virus titer, and this is probably due to the neutralization action of the antibody.

TABLE 1

| Treatment of Molt-4/HTLV-III with anti-HIV antibody | Specimen treated with | HIV Infectivity (log$_{10}$ TCID$_{50}$/ml) | |
|---|---|---|---|
| | | Medium | Cell |
| − | Lip(Fr.A) | 9.1 × 10$^4$ | 6.3 × 10$^4$ |
| − | Lip + Fr.A | 2.0 × 10$^6$ | 6.3 × 10$^6$ |
| − | Lip | 3.6 × 10$^5$ | 6.3 × 10$^6$ |
| − | Fr.A | 3.6 × 10$^5$ | 6.3 × 10$^6$ |
| − | PBS | 6.3 × 10$^5$ | 4.3 × 10$^6$ |
| + | Lip(Fr.A) | 1.2 × 10$^4$ | 2.0 × 10$^5$ |
| + | Lip + Fr.A | 6.3 × 10$^4$ | 4.3 × 10$^6$ |
| + | Lip | 4.3 × 10$^4$ | 9.1 × 10$^6$ |
| + | Fr.A | 3.6 × 10$^4$ | 6.3 × 10$^6$ |
| + | PBS | 6.3 × 10$^4$ | 6.3 × 10$^6$ |

(*)Lip(Fr.A), liposomes containing fragment A; Lip + Fr.A, mixture of liposomes not containing fragment A (i.e. empty liposomes) and fragment A; Lip, liposomes not containing fragment A (i.e. empty liposomes); Fr.A, fragment A.

What is claimed is:

1. A method for the treatment of acquired immunodeficiency syndrome (AIDS) which comprises administering a therapeutically effective amount of liposomes containing a fragment A of diptheria toxin which specifically inhibits the protein synthesis in cells to a patient with AIDS.

2. A method according to claim 1, wherein the administration is performed intravenously.

3. A therapeutic agent useful for the treatment of acquired immunodeficiency syndrome (AIDS) which comprises liposomes containing a fragment A of diptheria toxin which specifically inhibits the protein synthesis in cells.

4. A method of killing HIV-infected or HIV producing cells which comprises contacting said cells with liposomes containing a fragment A of diptheria toxin which specifically inhibits the protein synthesis in cells.

5. A method for the treatment of acquired immunodeficiency syndrome (AIDS) which comprises administering a therapeutically effective amount of liposomes containing a fragment A of diptheria toxin which specifically inhibits the protein synthesis in cells to a patient with AIDS, wherein said liposomes are administered in combination with azidothimidine (AZT).

* * * * *